United States Patent [19]

Kung et al.

[11] Patent Number: 4,962,765

[45] Date of Patent: * Oct. 16, 1990

[54] DIAGNOSTIC TEMPERATURE PROBE

[75] Inventors: Robert T. V. Kung, Andover; Timothy E. Moutafis, Gloucester; Burt D. Ochs, North Andover, all of Mass.

[73] Assignee: Abiomed, Inc., Danvers, Mass.

[*] Notice: The portion of the term of this patent subsequent to May 23, 2006 has been disclaimed.

[21] Appl. No.: 166,961

[22] Filed: Mar. 11, 1988

Related U.S. Application Data

[63] Continuation-in-part of Ser. No. 25,164, Mar. 12, 1987, Pat. No. 4,832,599.

[51] Int. Cl.$^5$ .................................................. A61B 5/00
[52] U.S. Cl. ...................................... 128/736; 433/32; 374/155
[58] Field of Search ..................... 128/736; 433/32, 27, 433/72, 75, 147, 127; 374/141, 155, 183, 185, 201

[56] References Cited

U.S. PATENT DOCUMENTS

| | | | |
|---|---|---|---|
| 3,552,210 | 1/1971 | Wright | 374/184 X |
| 3,935,640 | 2/1976 | Cohan | 433/75 |
| 4,280,508 | 7/1981 | Barrada | 128/736 |
| 4,379,461 | 4/1983 | Nilsson et al. | 128/736 |
| 4,501,555 | 2/1985 | Ditchborn | 433/72 X |
| 4,537,573 | 8/1985 | Sunada | 433/32 |
| 4,580,909 | 4/1986 | McIntosh | 374/208 X |
| 4,614,443 | 9/1986 | Hamert | 374/208 X |

FOREIGN PATENT DOCUMENTS 2448714 of 1980 France .
59-18425 1/1984 Japan .

OTHER PUBLICATIONS

*Does a Temperature Gradient Exist Across the Mucogingival Junction?* N. Brill, et al., Journal of Oral Rehab. 1978, vol. 5, pp. 81–87.
*The Temperature of the Gingival Sulci.* S. Mukherjee, J. Periodontal, v. 49, No. 11, Nov. 1978, pp. 580–584.

Primary Examiner—Max Hindenburg
Assistant Examiner—John P. Lacyk
Attorney, Agent, or Firm—Lahive & Cockfield

[57] ABSTRACT

A periodontal probe has a probe finger extending from a handle to an L-shaped distal end which includes a tip adapted for insertion into a periodontal pocket and formed of a thermally insulative material. A temperature sensing element is mounted at the extreme end of the tip. Conductive leads extend from the sensing element, through the probe tip to the handle. In a preferred embodiment, the temperature sensor is a thermocouple or thermistor, and the tip is sealed within an epoxy outer skin. The tip tapers so that the thermal mass of the probe in the vicinity of the sensing element quickly attains the temperature of surrounding tissue while minimally perturbing that temperature. The handle may contain signal processing or temperature display units, and the probe tip preferably includes graduations for indicating probe depth. Interchangeable sensor matching circuit elements adapt sensor elements having different characteristics to a common display driver. A system includes a probe and a processor with a display which indicates periodontal site locations to prompt entry of temperature measurements and to display disease indications based on those measurements. The temperatures are processed and are compared to stored tables of temperature difference distributions, to provide site-specific tissue diagnosis.

16 Claims, 5 Drawing Sheets

DIAGNOSTIC TEMPERATURE PROBE

REFERENCE TO PRIOR APPLICATION

This application is a continuation-in-part of prior U.S. patent application Ser. No. 025,164 filed Mar. 12, 1987, now U.S. Pat. No. 4,832,599 the priority of which is hereby claimed.

The present invention relates to clinical periodontal instruments, and to the diagnosis of periodontal disease.

It is known in medicine generally to diagnose certain conditions of internal infection or inflammation by sensing the distribution of temperature over regions of the body, and identifying regions of abnormally high temperature as affected.

Some researchers have made measurements of periodontal pocket temperatures, which appear to vary greatly. Because of this large variation, one might expect a temperature-plotting approach to be of limited diagnostic utility in periodontics.

Owing to the physiological structure of the jaw, there are temperature gradients from posterior to anterior regions, and from buccal to lingual sites on each side of the jaw. The presence of surface cooling due to breath air flow may further complicate the determination of even a normal temperature distribution. The combined effect of these sources of temperature variation is to mask from observation temperature anomalies which are less than approximately one-half degree Celsius. This would appear to limit the clinician's ability to identify with precision sites having temperature anomalies.

SUMMARY OF THE INVENTION

The present invention overcomes the foregoing limitations of the prior art by providing a periodontal probe having a handle and a probe finger extending from the handle to an L-shaped distal end. The distal end includes a probe stem portion adapted for insertion into a periodontal pocket and formed of a thermally insulative material, and a temperature sensing element mounted at the extreme end of the stem portion. Conductive leads extend from the sensing element, through the probe tip to the handle. In one embodiment, the temperature sensor is a thermistor which, together with the probe stem portion, is sealed within an epoxy outer skin. The tip tapers to approximately (0.016) inches diameter, so that the thermal mass of the probe in the vicinity of the sensing element quickly attains the temperature of surrounding tissue while minimally perturbing that temperature. A prototype attains 0.10 ° C. accuracy with a 0.2 second response time.

In an illustrated prototype, the handle contains signal processing and temperature display units. Preferably, the probe tip includes graduations for indicating probe depth. Preferred signal processing circuitry includes sensor matching circuit elements, for adapting sensor elements having different characteristics to a common display driver.

With such a measurement instrument, it has been possible to accurately chart the variations in temperature of a normal mouth as a function of position.

In another preferred embodiment, the handle includes a control button for initiating a temperature measurement, and a microprocessor processes the sampled temperatures to detect diseased tissue. The processor includes means for processing temperature measurements, and means for determining a variation in temperature over a region of the mouth. A graphic display prompts entry of temperature measurements for different tissue sites, and the processor compares the measurements to a table of normal and anomalous jaw temperature distributions. The graphic display then indicates the health of the probed sites.

BRIEF DESCRIPTION OF THE DRAWINGS

These and other features of the invention will be understood from the following description of an illustrative embodiment, with reference to the drawings.

DESCRIPTION

Figure 1:
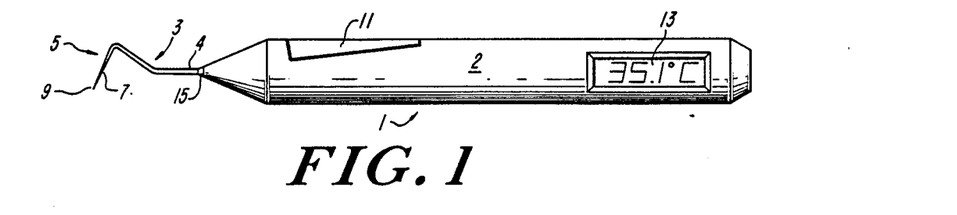
FIG. 1 shows a perspective view of a probe according to the invention.

FIG. 1 shows a perspective view of a prototype periodontal probe 1 according to the invention, having a handle portion 2 and a probe finger portion 3 extending from the handle. Finger portion 3 extends from a base end 4, which is firmly mounted in the handle, to a distal probe end 5 which has a general size and contour for probing a periodontal pocket.

At the distal end 5 of probe finger 3 a stem portion 7 having a length of approximately 1 cm. extends to a tip having a temperature sensing element 9 mounted thereat.

The overall length and shape of the probe 1 are substantially those of a Michigan "0" probe, and the base end 4 of the probe finger may be fabricated of metal. The handle 2, as discussed further below, houses signal conditioning and display circuitry for converting the temperature sensor output to a temperature display, and includes a power on switch 11 and three digit temperature display 13. Probe finger 3 attaches to handle 2 by a multi-contact electrical twist-connect fitting 15. Conductive leads (shown in FIG. 2A) extend from the temperature sensing element, through the stem and finger to the fitting 15.

The probe stem is formed of a material having low thermal conductivity, such as a polyimide or epoxy compound, thus isolating the temperature sensor from the main body of the probe finger. Preferably, the probe stem material has a thermal conductivity less than $10^{-2}$ watts/cm ° C. Applicant has found that the thermal conductivity of prior art probe fingers significantly perturbs the local temperature and limits the achievable accuracy of measurement and the response time.

Figure 2A:
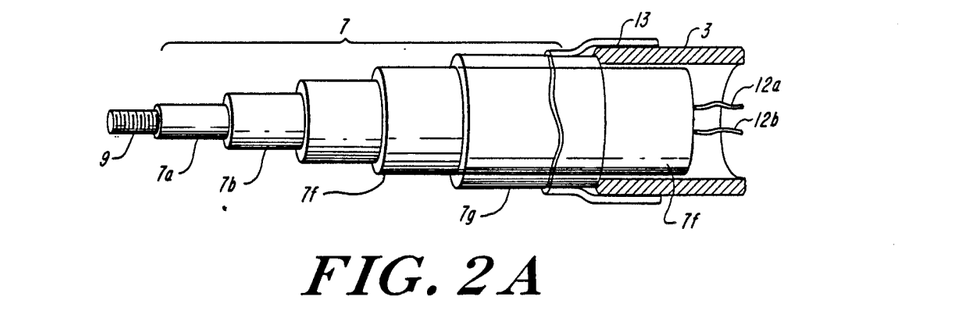
FIGS. 2A, 2B show details of the probe tip construction of one prototype probe similar to that of FIG. 1.

FIG. 2A shows a partial cutaway detail of construction of one probe tip having the desired strength and low thermal conductivity, employed in a prototype periodontal probe. As shown, finger portion 3 is formed from a 20 gauge thin-walled hypodermic needle, and stem portion 7 is made of a plurality of telescoping tubing segments 7a, 7b . . . 7f, 7g formed of a commercially-available polyimide tube stock. The largest tube has a diameter of approximately (0.036) inches and forms a shoulder against the end of the metal needle 3, and one or more of the smaller tube segments 7f . . . extends into needle 3. The telescoping tube segments form a stem which tapers from approximately (0.036) inches down to approximately (0.014) inches at the sensor end. Sensor 9 fits into the central bore of the smallest tube segment 7a.

During assembly, the conductive leads 12a, 12b of the sensor assembly 9 are passed through each tube as the tube segment is placed over the preceding segment. The wires are then passed through the bore of the needle 3, and cement is placed about the protruding portion of tube 7f and shoulder of tube 7g to secure the stem assembly into the needle. A thin plastic tube segment 13, which may be, for example, (0.002) inch mylar is then heat-shrunk about the stem-finger joint to secure the components during further assembly.

Figure 2B:
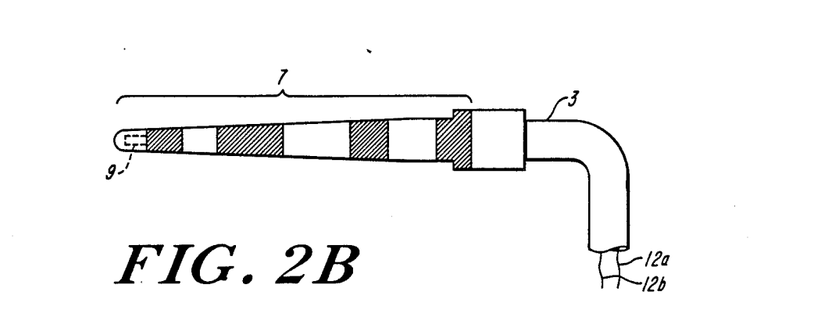

FIG. 2B shows the probe stem and tip assembly of FIG. 2A after such fabrication. The telescoping tapered stem and sensor unit 7, 9 is potted to form an epoxy-sealed assembly. One suitable epoxy is the epoxy resin sold as Shell 828, with a Versamid 140 hardener. Following potting, Williams markings are painted on the sealed, tapered stem assembly to show depth of penetration of the sensor 9, which is indicated in phantom. As shown, the markings are graduated to one centimeter, although longer probes may be constructed.

Figure 3:
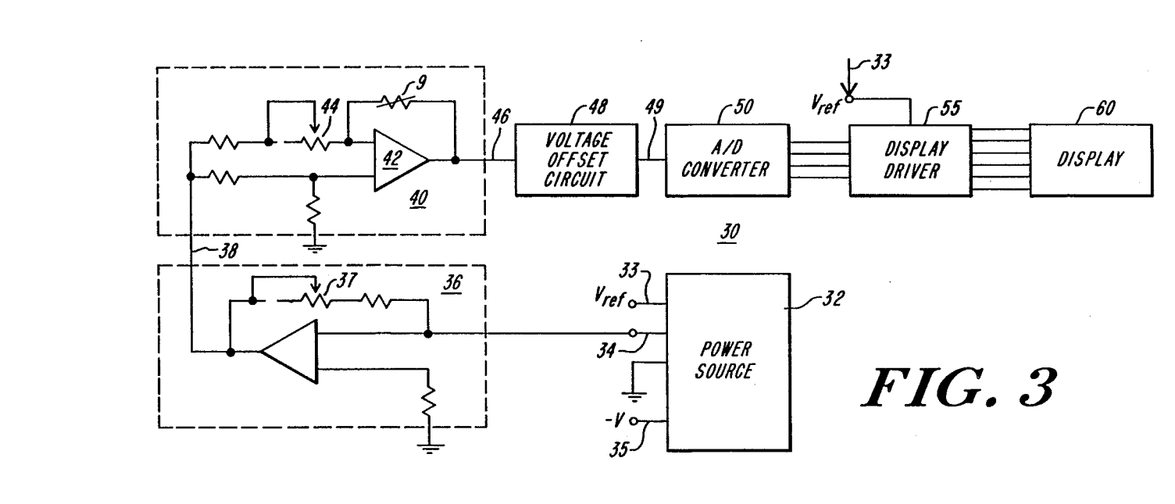
FIG. 3 is a schematic diagram of temperature sensing and display circuitry.

FIG. 3 shows a block diagram of a circuit 30 used in a prototype embodiment of the probe. Circuit 30 includes a power supply 32, which provides a fixed reference voltage at output 33 and voltages at outputs 34, 35 from a battery source. Voltage outputs 33, 344, 35 are achieved by providing a zener diode shunt to achieve a fixed voltage drop, which is then passed to a center-grounded voltage-dividing network in a manner known in the art. The drive voltage from output 34 passes to a voltage setting section 36 including an op amp with a feedback potentiometer 37 for adjusting amplifier gain so as to provide a selected stable output voltage along line 38.

The voltage on line 38 passes to a temperature sensing circuit 40 in which a second op amp 42 having a thermistor temperature sensor 9 in a feedback loop is adjusted, via second potentiometer 44 in a resistance bridge, so that the circuit 40 produces a zero volt output on line 46 when the thermistor 9 is at thirty seven degrees Celsius.

The potentiometers 37, 44 are adjusted upon assembly, with potentiometer 37 adjusted in accordance with the gain characteristics of sensing circuit 40—e.g., to provide a voltage which increases inversely to the nominal resistance of the selected thermistor 9—and with potentiometer 44 set such that a zero volt signal appears on line 46 at the desired nominal 37 degree temperature. The voltage on line 46 then varies, in a substantially linear fashion, as the temperature of the thermistor changes.

Thermistor 9 has a resistance in the range of 30–60 kilohms, and draws a steady state current which is sufficiently low to not perturb the temperature readings by internal heat generation. The temperature-indicative voltage signal on line 46 passes to a voltage offset circuit 48, which increments the voltage on line 46 by a fixed voltage offset to produce an offset temperature-indicating signal on line 49. The signal on line 49 is digitized and scaled with respect to the reference line 33 by an analog to digital converter 50, and the scaled digitized signal passes to a display driver 55 which drives a display 60. In the embodiment shown in FIG. 1, the display displays temperature readings in one-tenth degree increments.

In a preferred embodiment, the probe finger and tip assembly 3 as shown in FIG. 1 is a removably interchangeable tip assembly which connects to the handle 2 by an electrical-contact type twist lock connector. In that embodiment, the potentiometers 37, 44, which in the prototype are used to match the nominal resistance and resistance gradient characteristics of the thermistor so as to produce an accurately scaled voltage-to-temperature reading, are replaced by one or more fixed resistance pairs 37a, 44a, 37b, 44b, . . . , each pair being matched to the characteristics of a single thermistor tip assembly.

Figure 4:
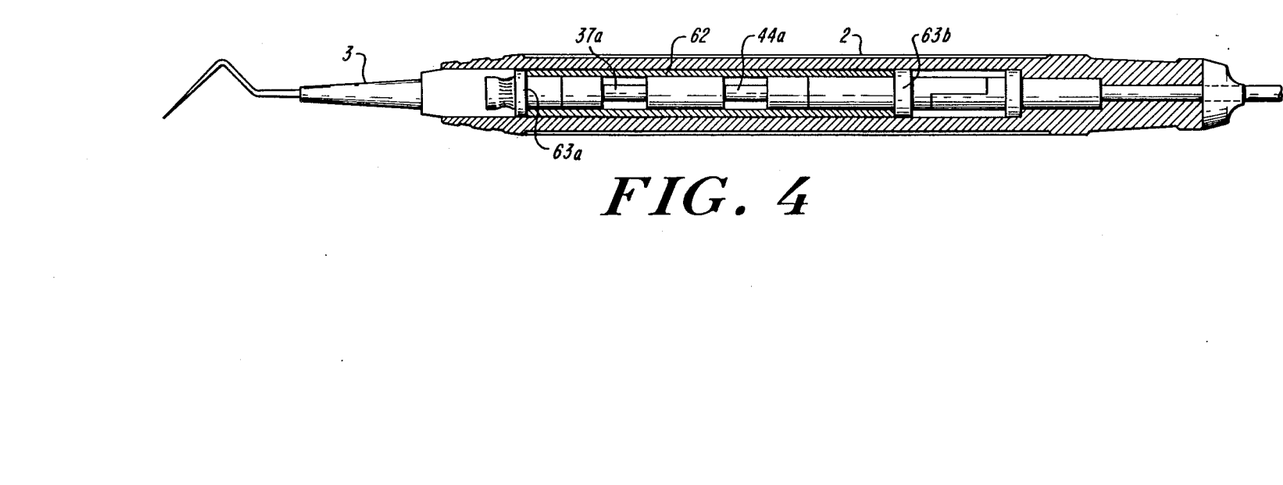
FIG. 4 is a section through a probe having interchangeable sensor units.

FIG. 4 shows a section through such a preferred embodiment. As shown, handle 2 contains a resistor cartridge 62 holding one or more pairs of matched resistors 37a, 44a, . . . . Cartridge 62 has a first end 63a adapted to engage the connector of probe tip 3, and a second end 63b which, upon engagement of the twist-locking probe tip connector places the correct pair of matched resistors into electrical contact with the voltage-setting and temperature-sensing circuitry. This allows replacement of tip assemblies, and permits the fitting of replacement temperature sensors, or temperature sensors adapted to detect finer temperature variations, or to accurately detect temperature variations centered about a different nominal center temperature.

Using a probe with a thermally isolated sensing end according to the invention accurate, repeatable measurements of periodontal pocket temperature have now been made. Analysis of such clinical measurements reveals that, with reference to the sublingual temperature of a subject, the periodontal temperature follows a predictable distribution which varies with the anatomic tooth location. Specifically, for a subject with healthy periodontal tissue, the temperatures of the periodontal pockets of upper jaw, or maxillary, teeth have been found to lie between (0.60) degrees and (2.53) degrees below the sublingual temperature as readings are taken of the third molar forward to the central incisor. Corresponding readings on the lower jaw, or mandibular, teeth vary between (0.06) and (1.19) degrees below the sublingual temperature. Generally, the temperature difference, referenced to sublingual, which is denoted $\Delta T$ herein, increases in magnitude from the back to the front of the jaw, from the lingual to buccal side of a given tooth, and between lower and corresponding upper jaw sites.

For each tooth location, a first temperature difference with respect to sublingual temperature, denoted $\Delta T'_H$ is a threshold indicative of healthy tissue, and a second, lesser magnitude temperature difference, denoted $\Delta T'_D$ indicates a higher temperature indicative of locally diseased tissue. Table 1 below shows a preliminary compilation of healthy and disease temperature difference thresholds used in a preferred diagnostic instrument to detect tissue health, as further described below.

TABLE I
ΔT THRESHOLDS

| | TOOTH | HEALTHY THRESHOLD $\Delta T'_H$ | DISEASED THRESHOLD $\Delta T'_D$ |
|---|---|---|---|
| Maxillary Upper Jaw | 3rd Molar | −0.60 | −0.22 |
| | 2nd Molar | −0.60 | −0.22 |
| | 1st Molar | −1.08 | −0.39 |
| | 2nd Bicuspid | −1.64 | −0.81 |
| | 1st Bicuspid | −2.09 | −1.16 |
| | Canine | −2.33 | −1.32 |
| | Lateral Incisor | −2.50 | −1.31 |
| | Central Incisor | −2.53 | −1.47 |
| Mandibular Lower Jaw | 3rd Molar | −0.06 | +0.06 |
| | 2nd Molar | −0.06 | +0.06 |
| | 1st Molar | −0.47 | −0.15 |
| | 2nd Bicuspid | −0.87 | −0.47 |
| | 1st Bicuspid | −1.13 | −0.60 |
| | Canine | −1.17 | −0.73 |
| | Lateral Incisor | −1.16 | −0.77 |
| | Central Incisor | −1.19 | −0.83 |

Figure 5:
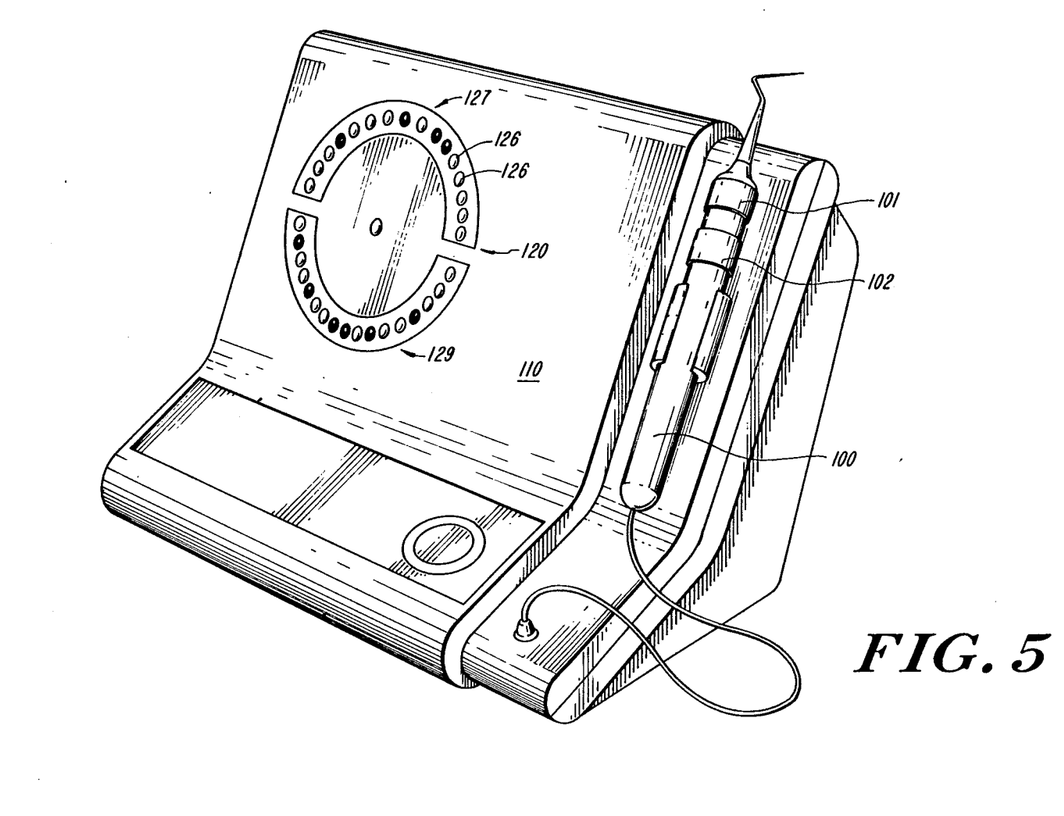
FIG. 5 shows a preferred clinical system embodying the invention.

According to another aspect of the invention, illustrated in FIG. 5, a system includes a temperature sensing probe 100 and a processing unit 110 connected to the probe for processing temperature signals developed by the probe. Unit 110 includes a display 120 in the form of a map 125 of the jaw. Map 125 includes a plurality of light emitting diodes 126 (LEDs) with each diode position corresponding to one tooth location on the upper 127 or lower 129 jaw. A central diode 130 represents the sublingual region. As described more fully below, the LEDs are multi-color LEDs which may each be actuated to provide two, and preferably three, color indications. The handle of probe 100 includes two actuation buttons, 101, 102 denoted the "enter" and "advance" buttons, coupled to the processing unit as described below.

Figure 8:
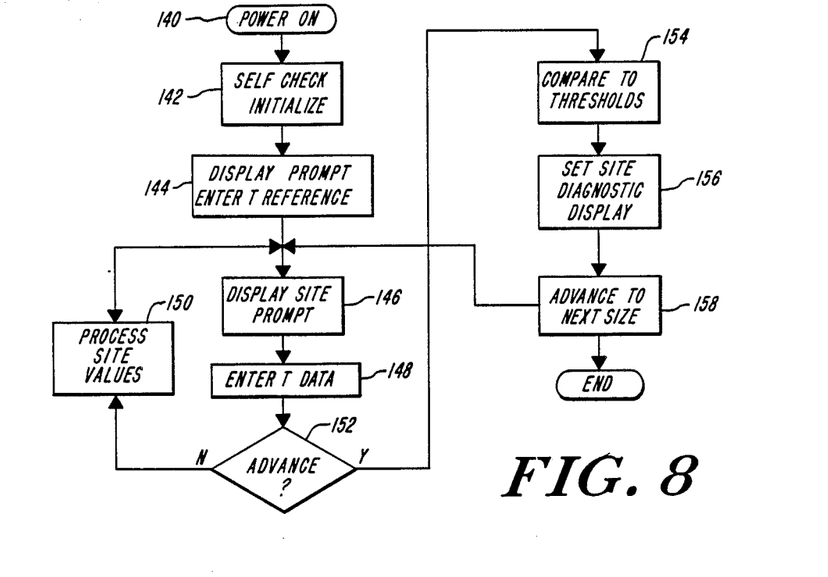
FIG. 8 shows a flow chart of a microprocessor-based clinical system as illustrated in FIG. 5.

Operation of unit 110 is illustrated by the flowchart, FIG. 8. Unit 110 includes a microprocessor having a ROM table memory which stores a set of temperature difference thresholds as shown in Table 1 above, and includes polling and arithmetical processing units for converting successive probe readings to temperature values, means for associating such readings with tooth locations, and means for deriving the measured ΔT value for a location and comparing it to the stored thresholds to determine when a periodontal pocket is diseased.

After turning on the power at step 140, the processor loads an instruction set, initializes its registers and performs a self check 142. The self check ascertains that all LEDs are operative, that probe leads are connected, and that the operating program is properly initialized.

At 144, the processor then actuates a display driver to prompt the operator to enter the reference site temperature. In the illustrated embodiment, the central diode 130 is intermittently actuated as a blinking green light to instruct the operator to enter the sublingual temperature by placing the probe tip below the subject's tongue and pressing the enter button 101 (FIG. 5). Following entry of one or more sublingual temperature measurements, the advance button 102 is pressed, and the entered temperatures for that site are processed to determine an average sublingual temperature which is stored as a reference temperature against which subsequent periodontal temperature differences are determined.

The processor at 146 then connects the display driver to the LED of a next tooth location (e.g., the left upper third molar) to prompt the operator to place the probe at sites around that tooth, and polls the probe to determine when the "enter" and "advance " buttons are pressed. Each time the "enter" button 101 is pressed, a temperature reading is taken and processed at step 150. The invention contemplates operation in several processing modes, including a mode wherein successive measurements at a single site or sites around a tooth are averaged to eliminate random measurement variations.

During data entry at a tooth, the LED associated with that tooth blinks indicating to the operator the present sampling location. Next at 152 the operator presses the advance button 102. This turns off the blinking LED and initiates arithmetical processing wherein the processed site value is subtracted from the sublingual reference temperature to determine ΔT for that site. At step 154, this ΔT value is compared to the stored table of threshold healthy and diseased temperature differences for the indicated jaw location. Based on this comparison, the sampled site is classified as healthy (H), diseased (D) or indeterminate (I). At step 156 the display for that site is actuated to display an H, D or I indication, and this display is thereafter maintained on the corresponding LED 126 as the processor advances its polling to the next tooth (left upper second molar, in this example) and repeats loop 160.

In the prototype embodiment, LED s 125 are two-color LEDs. Actuation with a first voltage signal drives a red display, and actuation with a second voltage signal drives a green display Simultaneous actuation of red and green produces a Yellow light. The red and green colors are used to indicate (D) and (H) states respectively, with yellow indicating indefinite diagnosis (I).

After the operator has performed measurements on one or more tooth location by pressing the advance button to cycle through the successive jaw locations, the display continues to show the (D), (H) or (I) determinations for all sites tested. Repeat or replacement measurements if desired can be performed for one or more selected teeth by advancing to those teeth and entering new data. These diagnoses may then be checked off by the operator on a conventional printed jaw chart, or optionally may be printed out, together with actual temperature measurements if desired, for record purposes.

For the processing of measured temperatures, two basic operations are performed, designated mode 1 and mode 2. In mode 1, the periodontal site temperature T for a tooth is compared to the sublingual temperature $T_S$ to develop the difference $\Delta T = T - T_S$, which is typically less than zero. If $\Delta T < \Delta T'_H$, the stored "healthy threshold" for the tooth, the site is deemed healthy; if $\Delta T > \Delta T'_D$ the "disease threshold", the site is deemed diseased. If ΔT lies between the two, i.e., $\Delta T'_H \leq \Delta T \leq \Delta T'_D$ the site is deemed indefinite and no definite diagnosis is given.

Figure 9:
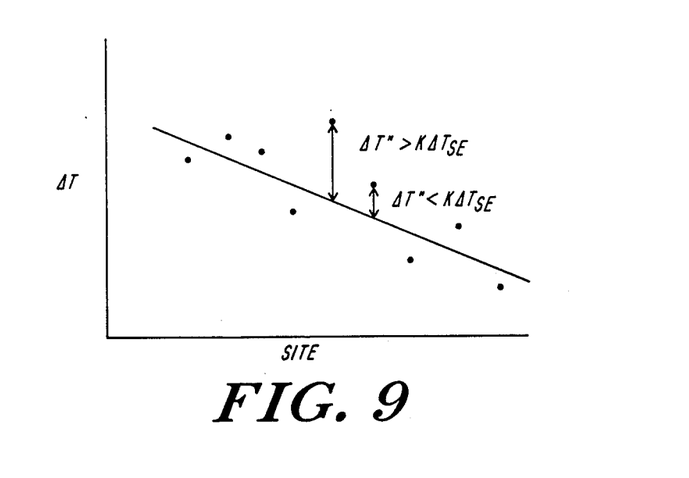
FIG. 9 shows a representative temperature analysis using a stored table of variations.

In mode 2 the temperatures are processed in a block. A number, e.g., nine site readings are queried on three adjacent teeth, with three sites (either all lingual or all buccal) on each tooth referenced to the sublingual temperature. A numerical processor performs a linear regression fit on the nine temperature measurements to obtain a best fit curve representing ΔT in the three-tooth region. FIG. 9 shows such a graph ΔT in relation to nine sample points. The distances ΔT" of each temperature sample point from the graph is then formed, and is compared to a standard "error of estimate" value $\Delta T_{SE}$ which has been compiled on a tooth-by-tooth basis from healthy subjects and is stored as a second table. The healthy/diseased diagnosis may be made based on whether $\Delta T''$ is less than or greater than $K \Delta T_{SE}$, where K is a constant, which may be between one and two, the value of which is selected in accordance with a desired sensitivity of the determination. Other detection modes embodying different temperature comparisons are also contemplated.

Figure 6:
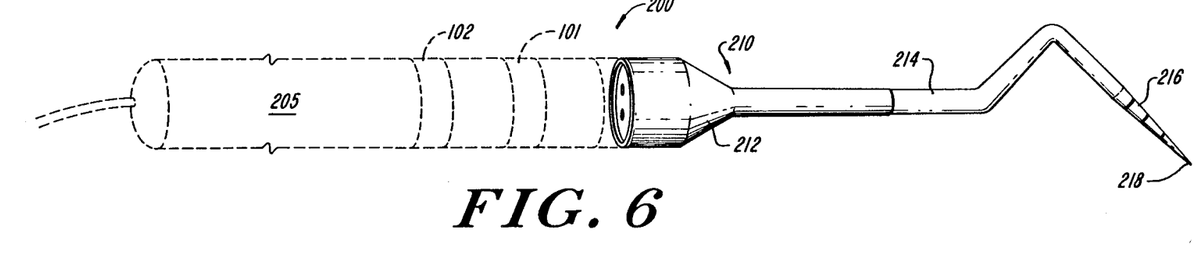
FIG. 6 shows another probe with a replaceable sensing tip.
Figure 7:
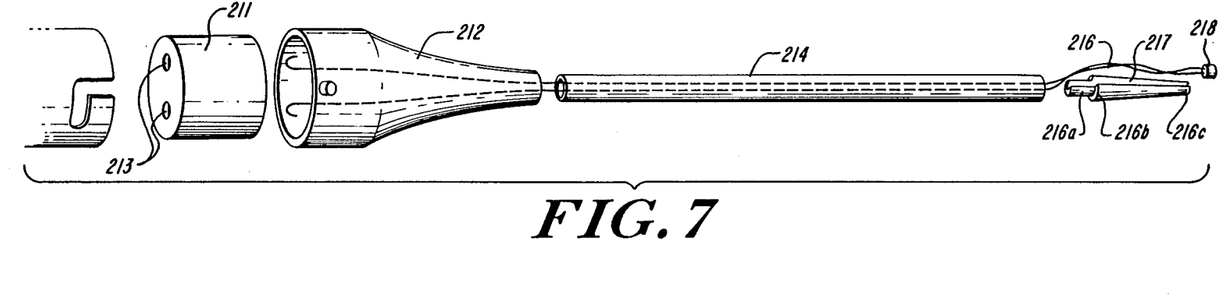
FIG. 7 shows the probe tip of FIG. 6 at an earlier stage of manufacture and assembly.

Returning now to the probe construction, FIGS. 6 and 7 illustrate the structure and manufacture of a presently preferred probe 200 having the same overall size and shape as the probe 1 of FIG. 1, and especially suitable for the system of FIG. 5.

Probe 200 includes a handle 205, which may include circuitry a indicated in the probe of FIG. 1 for converting a temperature sensor signal to a digital signal, and contains pushbutton "enter" and "advance" switches 101, 102 discussed above (not illustrated). A tip assembly 210 removably attaches to the handle and contains a temperature sensing element at the end thereof. Tip assembly 210 is fabricated as a disposable element of simplified construction. As shown, tip assembly 210 comprises four major portions, a shank 212, a tubular finger 214, a graduated tip 216 and an electrosensing temperature element 218, which extend successively away from the handle.

FIG. 7 shows a disassembled perspective view, partly in phantom, of these elements at an early stage of assembly. Shank 212 is a molded plastic body, formed of Delrin, Nylon, ABS or similar tough polymer. Tubular finger 214 is formed of 20-gauge thin walled stainless steel stock. At the assembly stage finger 214 is a straight tube of approximately 3 cm. length; upon completion of assembly the tube is bent to provide the characteristic periodontal probe Z-shape of FIGS. 1, 5. Tip or nosepiece 216 is formed of polysulfone or a similar strong polymer having low thermal conductivity, and has a slot 217 therein so that the conductive leads of sensor 218 may be conveniently channeled therethrough. After placement of the sensor 218 at the tip of piece 216 and threading the sensor leads through tube 214 and shank 212, the parts are cemented and pressed together, and tip 216 is dipped in epoxy, and cured, and the bands are printed thereon. Finally, a rubber bushing 211 with conductor receptacles 213 is fitted in shank 212 to provide a plug-like connection to the tip.

The tapered tip 216 has overall dimensions similar to those described for the multi-piece polymide tube embodiment of FIGS. 2A, 2B, tapering from about (0.035) inches at its trunk $216b$ to approximately 0.016 inches diameter at the sensor end $216c$. A short stem portion $216a$ is dimensioned to press fit within tube 214 for assembly. Polysulfone material has been found to possess suitable strength for this part of these dimensions, and exhibits thermal conductivity of approximately $1 \times 10^{-3}$ watts/cm. ° C, with flexural modulus and flexural yield strength of $4 \times 10^5$ and $1.5 \times 10^4$ psi respectively. Other materials such as polyimides, polyamide/imides, and materials with similar properties may be used, to effectively provide a low mass thermally isolated sensor tip. Sensor element 218 is preferably a copper-constantin thermocouple It will be appreciated that the foregoing periodontal probes and systems have been described with reference to illustrated prototype embodiments and preferred variations thereof, but that the invention is not limited thereto. In other embodiments, different temperature sensing elements, different signal conditioning circuitry and different measurement processing may be employed, and different probe finger constructions and fittings are possible. The invention being thus disclosed, further variations will occur to those skilled in the art, and such variations are within the spirit of the invention, as defined by the following claims.

What is claimed is:

1. A clinical temperature sensing probe assembly comprising:
    a shank portion which serves as a handle or as a connector for attachment to a handle, and
    a tip portion extending from the shank portion, including
    a first thin elongate member extending from the shank portion to a distal end, and
    a thermally insulating penetrating tip extending from said distal end, said tip having a shape adapted for penetrating a periodontal pocket to position a temperature sensing element therein, and
    a temperature sensing element mounted at the end of the penetrating tip to be positioned in the pocket and sense temperature at a pocket location without inducing temperature perturbations.

2. An assembly according to claim 1, wherein said tip is a tapered tip formed of material having a thermal conductivity less than approximately $10^{-2}$ watt/cm. °C.

3. A periodontal probe of the type having a handle with a projecting finger-shaped probe tip for insertion into a periodontal pocket, wherein the probe tip comprises a thermally insulative stem having a thermal conductivity below $10^{-2}$ watts/cm C°, a temperature sensing element supported at an end of the probe tip by the stem, and a signal-conducting lead extending from said temperature sensing element through said stem to said handle, said thermally insulative stem having a shape and size to penetrate a periodontal pocket and position the temperature sensing element therein to effect periodontal pocket measurements insulated from temperature perturbations of surrounding material.

4. A temperature measuring instrument for clinical diagnosis comprising
    a hand-held temperature probe having a temperature sensing tip adapted for insertion into body tissue,
    a processor in circuit communication with said probe for receiving temperature information therefrom,
    a display controlled by said processor said display including an array of lights arranged as a map of discrete tissue locations,
    means for actuating said display to prompt a user to insert the probe at a tissue location identified by a light on the map for measuring the temperature thereof, and
    means for determining as a function of tissue location whether the measured temperature is representative of a healthy or diseased tissue state,
    said means for determining being operatively connected to said means for actuating such that a light of said array is actuated to indicate said state.

5. An instrument according to claim 1, wherein the temperature probe is a periodontal probe having a temperature sensor at a tip thereof.

6. An instrument according to claim 1, wherein said processor includes means for comparing a measured temperature characteristic of a tissue location to a reference temperature characteristic measured as a fixed tissue site.

7. An instrument according to claim 6, wherein said processor includes a stored table of characteristic site temperature difference values, and also includes means for comparing a measured tissue site difference with a said value for determining tissue site health.

8. An instrument according to claim 6, wherein said processor includes a stored table of characteristic variations of tissue site differences, and also includes means for comparing a measured variation with a characteristic tissue site difference for determining tissue site health.

9. An instrument according to claim 6, wherein said display includes a plurality of LEDs arranged as a map of sites of body tissue, and wherein said processor controls the states of said LEDs in accordance with the measurement of site temperatures and determinations of tissue state.

10. An instrument according to claim 6, wherein said probe includes a probe finger extending to a tapered tip portion having a temperature sensing element mounted at the outer end of the tip, said outer end being adapted for insertion into a periodontal pocket, and wherein said tapered tip portion is formed of low thermal conductivity material for thermally isolating said element.

11. An instrument according to claim 10, wherein said tip portion includes an epoxy, a polysulfone, a polyimide or a polyamide/imide material.

12. An instrument according to claim 11, wherein said temperature sensing element is a thermocouple.

13. An instrument according to claim 1, wherein said array of lights includes lights of plural colors for each tissue location, and said means for determining is operative to actuate different color lights for indicating healthy or diseased states.

14. An instrument according to claim 13, wherein a green light indicates a healthy state and a red light indicates a diseased state.

15. An instrument according to claim 6, wherein said probe is adapted for insertion into a periodontal pocket and said processor compares periodontal pocket temperatures to a reference temperature measured at a sublingual site.

16. An instrument according to claim 1, further comprising means for printing an indication of said state.

* * * * *

UNITED STATES PATENT AND TRADEMARK OFFICE
CERTIFICATE OF CORRECTION

PATENT NO. : 4,962,765

DATED : October 16, 1990

INVENTOR(S) : Kung et al.

It is certified that error appears in the above-identified patent and that said Letters Patent is hereby corrected as shown below:

Column 8, line 58, please replace "claim 1" with --claim 4--.

Column 8, line 61, please replace "claim 1" with --claim 4--.

Column 10, line 19, please replace "claim 1" with --claim 4--.

Signed and Sealed this

Twenty-eighth Day of July, 1992

Attest:

DOUGLAS B. COMER

*Attesting Officer*     *Acting Commissioner of Patents and Trademarks*

UNITED STATES PATENT AND TRADEMARK OFFICE
CERTIFICATE OF CORRECTION

PATENT NO. : 4,962,765
DATED : October 16, 1990
INVENTOR(S) : Kung et al.

It is certified that error appears in the above-identified patent and that said Letters Patent is hereby corrected as shown below:

Column 3, line 37, please replace "outputs 33, 344, 35" with --outputs 33, 34, 35--.

Column 6, line 6, after "successive" please insert --temperature--.

Column 7, line 61, after "thermocouple" please insert --.--.

Signed and Sealed this

Twenty-fourth Day of November, 1992

*Attest:*

DOUGLAS B. COMER

*Attesting Officer*     *Acting Commissioner of Patents and Trademarks*